(12) United States Patent
Skigen

(10) Patent No.: US 9,486,543 B2
(45) Date of Patent: *Nov. 8, 2016

(54) ORAL ANESTHESIA APPLICATION

(71) Applicant: Andrew L. Skigen, Jacksonville, FL (US)

(72) Inventor: Andrew L. Skigen, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,063

(22) Filed: Oct. 20, 2015

(65) Prior Publication Data
US 2016/0038614 A1    Feb. 11, 2016

Related U.S. Application Data

(63) Continuation of application No. 13/732,408, filed on Jan. 1, 2013, now Pat. No. 9,192,572.

(60) Provisional application No. 61/582,453, filed on Jan. 2, 2012.

(51) Int. Cl.
*A61K 49/00* (2006.01)
*A61K 9/00* (2006.01)
*A61K 9/70* (2006.01)
*A61K 31/167* (2006.01)
*A61K 31/245* (2006.01)

(52) U.S. Cl.
CPC ............ *A61K 49/006* (2013.01); *A61K 9/006* (2013.01); *A61K 9/0056* (2013.01); *A61K 9/7007* (2013.01); *A61K 31/167* (2013.01); *A61K 31/245* (2013.01); *A61K 9/0034* (2013.01)

(58) Field of Classification Search
CPC .... A61K 9/0056; A61K 9/707; A61K 9/006; A61K 9/0034
See application file for complete search history.

*Primary Examiner* — Suzanne Ziska
(74) *Attorney, Agent, or Firm* — Joseph P. Kincart; Rogers Towers PA

(57) ABSTRACT

The present invention provides a device for administering an active agent to a localized mucous membrane in the oral cavity of a mammal, as well as an oral dissolving film formed therefore.

19 Claims, 4 Drawing Sheets

301

302

```
┌─────────────────────────────────────────────────────────────┐
│   SELECTING AN MUCOSAL DISSOLVING FILM INCLUDING AN ACTIVE  │
│  401                        AGENT                           │
└─────────────────────────────────────────────────────────────┘
                              │
┌─────────────────────────────────────────────────────────────┐
│  IDENTIFY A SPECIFIC AREA IN CONTACT WITH MAMMALIAN MUCCOUS │
│  MEMBRANE SUCH AS THE ORAL CAVITY TO BE TREATED BY THE ACTIVE│
│  402                        AGENT                           │
└─────────────────────────────────────────────────────────────┘
                              │
┌─────────────────────────────────────────────────────────────┐
│   SHAPE ORAL DISSOLVING FILM TO A SIZE AND SHAPE FOR PLACEMENT│
│    ON THE MUCOUS MEMBRANE SUCH AS IN A MAMMALIAN ORAL CAVITY │
│  403                                                        │
└─────────────────────────────────────────────────────────────┘
                              │
┌─────────────────────────────────────────────────────────────┐
│    PLACE THE ORAL DISSOLVING FILM WITH AN ACTIVE AGENT ON THE│
│   SPECIFIC LOCATION TO BE TREATED IN CONTACT WITH THE MUCOUS│
│  404                                                        │
└─────────────────────────────────────────────────────────────┘
                              │
┌─────────────────────────────────────────────────────────────┐
│    TREAT THE SPECIFIC AREA IN MAMMALIAN MUCOUS MEMBRANE     │
│                    WITH THE ACTIVE AGENT                    │
│  405                                                        │
└─────────────────────────────────────────────────────────────┘
                              │
┌─────────────────────────────────────────────────────────────┐
│   ADMINISTER AN INJECTION INTO THE SPECIFIC AREA TREATED BY THE│
│                          ACTIVE AGENT                       │
│  406                                                        │
└─────────────────────────────────────────────────────────────┘
```

FIG. 4

ORAL ANESTHESIA APPLICATION

CROSS REFERENCE TO RELATED APPLICATIONS

The present application claims priority as a Continuation Application to U.S. patent application Ser. No. 13/732,408 entitled: Oral Anesthesia Application, filed Jan. 1, 2013, which in turn claims priority to U.S. Provisional Patent Application Ser. No. 61/582,453 filed Jan. 2, 2012, the contents of each are relied upon and incorporated herein by reference.

FIELD OF THE INVENTION

The present invention relates to methods and apparatus for topically applying medicaments within the human oral cavity. More specifically, the present invention presents methods an apparatus for providing anesthesia to the human gum or other oral tissue in a pain free fashion.

BACKGROUND OF THE INVENTION

Dental fear refers to the fear of dentistry and of receiving dental care. It is estimated that as many as 75% of US adults experience some degree of dental fear, from mild to severe. It is further estimated that some 5 to 10 percent of U.S. adult dental patients are considered to experience dental phobia wherein they become so fearful of receiving dental treatment that they avoid dental they have a dental emergency, such as a toothache or dental abscess. Women tend to report more dental fear than men, and younger people tend to report being more dentally fearful than older individuals. In addition People tend to report being more fearful of more invasive procedures, such as oral surgery which require anesthesia in order to manage pain, than they are of less painful treatments, such as professional dental cleanings, or prophylaxis.

Direct experience is the most common way people develop dental fears. Significant numbers of people report that dental fear is related to painful dental experience. Often a painful experience begins with administration of a local anesthetic via injection into very sensitive oral tissue, such as gum tissue. Once anesthesia is administered, patient pain may be controlled and proper dental care may be carried out.

What is needed therefore is a way to easily administer at least a first dose of local anesthesia in a manner which does not induce pain to the patient and therefore decrease the incidence of patient pain and patient anxiety.

Traditionally, oral dissolving films have not been helpful to address this problem. Although oral dissolving films have been known to be placed on a patient's tongue or any oral mucosal tissue. Such films are for systemic delivery of an active agent, entering the blood stream via the digestive track.

SUMMARY OF THE INVENTION

Accordingly, the present invention provides methods and products for painlessly administering anesthetic agents in very specific topical areas of the oral cavity. In particular, oral thin films are sized and shaped to adhere to areas of a mammalian gum and release an anesthetic agent to the area of the gum to which they are adhered. The oral thin films may include, for example, orally dissolving films (ODFs) which provide quick release of an active pharmaceutical ingredient (API) when placed on a moist mucosal surface.

One general aspect includes a device for relieving pain during a procedure on a specific area of a mammalian mucous membrane, the device including: an oral dissolving film including a non-toxic film of a suitable size and shape to be placed on the specific area of the mammalian mucous membrane in a mammalian oral cavity and which dissolves essentially in its entirety as a result of contact with secretions from the mucous membrane in the mammalian oral cavity; a local anesthetic active agent combined with the oral dissolving film such that the local anesthetic active agent comes into contact with the specific area of the mammalian mucous membrane in the mammalian oral cavity as the oral dissolving film dissolves and thereby treats a situs to receive the procedure; and a coloring agent also combined with the oral dissolving film such that the coloring agent comes into contact with tissue in the specific area of the mammalian mucous membrane in the mammalian oral cavity as the oral dissolving film dissolves on the mammalian mucous membrane.

Implementations may include one or more of the following features. The apparatus may include a device for relieving pain during the procedure on a specific site on a mammalian mucous membrane where a local anesthetic active agent may be combined with an oral dissolving film. The oral dissolving film may include a sufficient quantity to numb the specific area such that pain from procedure including an injection is diminished during administration of the injection. The device may also relieve pain during the procedure on a specific site on the mammalian mucous membrane where the local anesthetic active agent includes ethyl ester of p-aminobenzoic acid. The device may also relieve pain during the procedure on a specific site on the mammalian mucous membrane additionally including a sweetener. The device may also relieve pain during the procedure on the specific site on the mammalian mucous membrane where a visual indicator remains visible on an area of oral mucosa after the oral dissolving film dissolves essentially in its entirety. The device may also relieve pain during the procedure on the specific site on the mammalian mucous membrane where the visual indicator allows a practitioner to visually identify the area that has been treated by the local anesthetic and administer an injection into the area that has been treated by the local anesthetic with the oral dissolving film essentially dissolved in its entirety. The device may also relieve pain during the procedure on a specific site on the mammalian mucous membrane additionally including an aseptic package encompassing one or more oral dissolving films.

One general aspect includes a device for relieving pain relating to a condition on a specific area of mammalian mucous membrane. The device may include an oral dissolving film including a non-toxic film of a suitable size and shape to be placed on the specific area of the mammalian mucous membrane of a mammalian oral cavity. The dissolving film may dissolve essentially in its entirety as a result of contact with secretions from the mucous membrane in the mammalian oral cavity. The device may also include a local anesthetic active agent combined with the oral dissolving film such that the local anesthetic active agent comes into contact with the specific area of mammalian mucous membrane in the mammalian oral cavity as the oral dissolving film dissolves and treats a situs of discomfort including the specific area of mammalian mucous membrane. The device may also include a coloring agent also combined with the oral dissolving film such that the coloring agent comes into contact with tissue in the specific area of mammalian mucous membrane in the mammalian oral cavity as the oral dissolving film dissolves on the mammalian mucous membrane.

Unlike previously known applications which placed an orally dissolving thin film on a patient's tongue or other oral mucosal tissue for general administration of an active agent via the digestive canal. The present invention provides for rapid adherence of the film to mucosal tissue and direct administration of an anesthetic agent directly to the site of adherence. In general, the film is placed on a gum or other mucosal tissue and hydrated with saliva; the saliva hydration causes adherent forces to bind the specifically sized ODF on to a site of anesthetic application, or other delivery of an active agent. The anesthesia is administered directly into the adhesion site on the gum.

As the ODF dissolves, traditional local anesthesia, such as an injection of Novocain may be administered directly into the gum site that has been anesthetized by the anesthetic agent of the ODF.

BRIEF DESCRIPTION OF THE DRAWINGS

FIG. 4 illustrates method steps that may be practiced in some implementations of the present invention.

DETAILED DESCRIPTION

The present invention provides methods and products for locally administering one or more active agents to a mucous membrane such as, for example, mucous membrane included in a mammalian oral cavity. The active agent may include, for example an anesthetic. Some specific examples include an active agent including ethyl ester of p-amino benzoic acid (PABA), such as, for example, benzocaine. Other examples may include, but are not limited to: benzocaine,butamben, dibucaine, lidocaine, oxybuprocaine, pramoxine, proparacaine, proxymeta caine, and tetracaine (also named amethocaine). In general, according to the present invention, a film with an active agent is placed upon a mucous membrane and an area of the mucous membrane is anesthetized such that the procedure, such as an injection, may be administered to the anesthetized area.

Other exemplary areas of mammalian mucous membrane may include, but not be limited to a mammalian vaginal cavity. Other procedures may include a biopsy or other minor incision. A biopsy or incision may include, by way of example a cervical biopsy which may be painful without anesthesia.

Glossary

Orally Dissolving Films (sometimes referred to herein as "ODF") as used herein shall mean a non-toxic film which may be placed in an mammalian oral cavity and dissolve as a result of contact with saliva or other liquid on of secreted by the mucous membrane comprising the mammalian oral cavity.

In various embodiments, ODFs may contain, by way of teaching example one or more of: film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

An ODF according to the present invention may additionally include supplementary ingredients such as, by way of example: plasticizers, sweetening and flavoring agents, coloring agents, saliva-stimulating agents, and thickening agents. Inactive ingredients of may include: Methocel K3, Methocek K100, Methocel K4, Sodium Carboxymethyl Cellulose, Glycerine, Sucralose, Polysorbate 80, Peppermint Oil Flavor, Gum Arabic, Sodium Copper Chlorophylin.

Oral Cavity Based Size and Shape (sometimes referred to herein as "OCBSS) as used herein shall mean a size and shape of an ODF suitable for placement on the surface of a mucous membrane and/or gum comprising a mammalian oral cavity.

Figure 1:
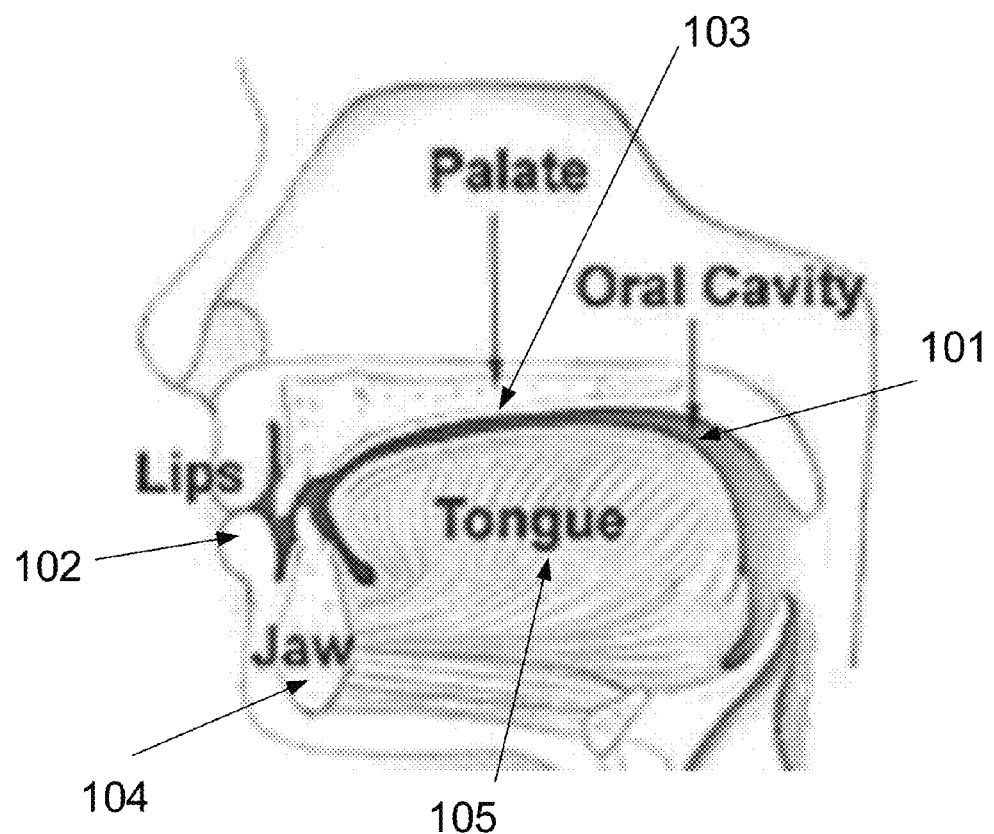
FIG. 1 illustrates an oral cavity in which the present invention may be implemented.

Referring now to FIG. 1, a cutaway of a profile of a mammalian oral cavity 101 (as illustrated a human oral cavity) is illustrated. The mammalian oral cavity 101 may be bordered for example by a set of lips 102, a palate 103 and a jaw 104. The mammalian oral cavity will also contain a tongue 105, and gums and teeth (illustrated in FIG. 2).

Figure 2:
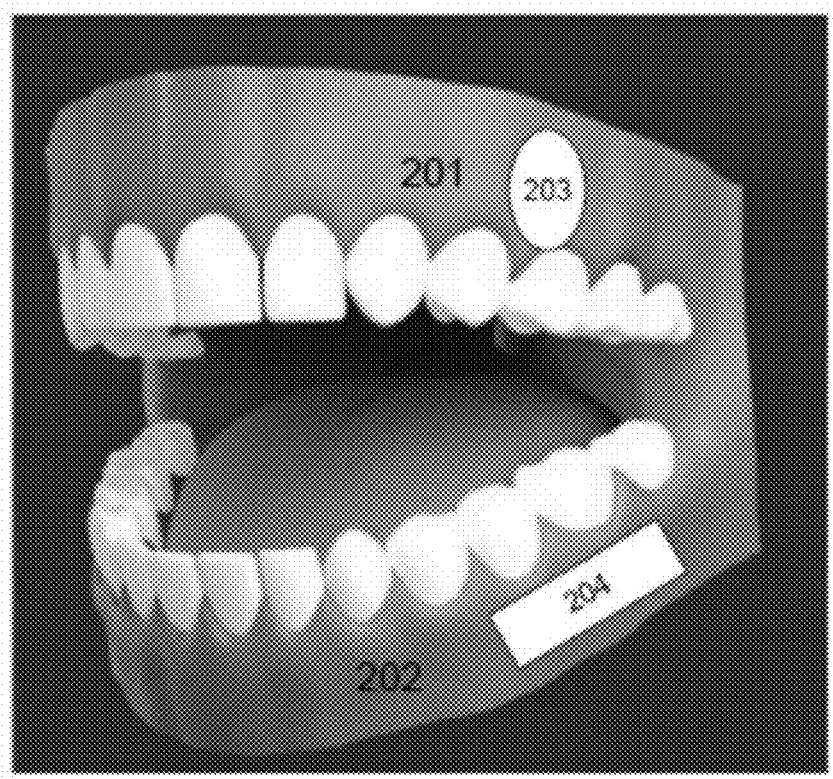
FIG. 2 illustrates a human upper gum and lower gum with locally administrating ODF strips according to some embodiments of the present invention.

Referring now to FIG. 2, a perspective view of human upper gums 201 and lower gums 202 are shown. As illustrated, the human upper gums 201 have an oval shaped ODF 203 placed on gum surface. In addition, the lower gums 202 have a rectangular ODF placed upon the gum surface. As illustrated, each of the oval shaped ODF 203 and the rectangular shaped ODF 204 are Oral Cavity Based Size and Shape since each sits on a gum and do not protrude beyond a gum line on to the teeth.

Figure 3:
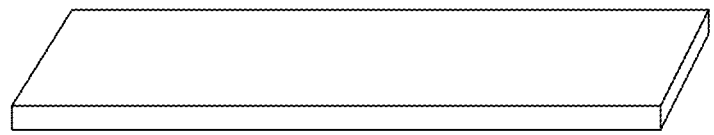
FIG. 3 illustrates rectangular shape and oval shape implementations according to some embodiments of the present invention.
Figure 3:
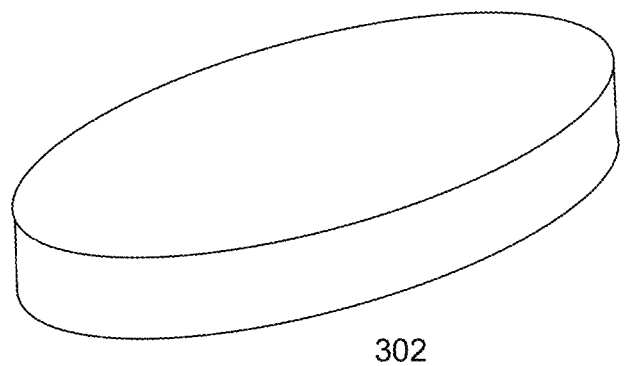

Referring now FIG. 3, perspective views of exemplary shapes of Oral Cavity Based Shapes are illustrated. Illustrated shapes include, by way of example, rectangular 301 and oval 302. Other shapes are also within the scope of the present invention. In some embodiments, an ODF may be one or both of: shaped and sized with a scissor prior to placement on a gum or mucous membrane. Placement may be accomplished via a human finger or a swab or other instrument.

Referring now to FIG. 4, exemplary steps that may be practiced in some embodiments of the present invention are illustrated. The steps are presented in a logical order for some embodiments, however, the order presented is by way of example only and not meant to limit the scope of the invention. At 401, an active agent may be included in an ODF. At 402, a specific location or area within a mammalian cavity to be anesthetized or otherwise treated by an active agent included within the ODF. At 403, the ODF may be sized and shaped such that it is suitable for placement on the specific location or area identified. At 404, the ODF which has been shaped is placed at the desired location to be treated. At 405, the specific location or area in the mammalian oral cavity which be treated received the effect of the active agent.

At 406, an injection may be administered into the specified area. In some embodiments, an injection may include additional anesthesia.

In some embodiments, the ODF includes an active agent which includes a pharmaceutical ingredient. The pharmaceutical ingredient may be absorbed at the specified location for local oral administration as opposed to systemic active pharmaceutical ingredient.

According to some embodiments, the active pharmaceutical ingredients may include those known to topically treat oral conditions such as, by way of non-limiting example, one or more of: anesthetics, antifungal; antiseptics; and topical steroids.

According to the present invention, the nature of the film that is included in the ODF fixates the location of active pharmaceutical ingredient, eliminating migration, dissipation and dilution. The adhesion may be described as muco-adherence, wherein muco-adherence allows for a lower concentration of a given active pharmaceutical ingredient to be used to achieve a desired amount of anesthetic action and/or a desired health benefit.

Generally, lower concentration of an active agent may be beneficial due to a decrease in deleterious systemic side effects of excessive active pharmaceutical ingredient absorption such as methemaglobinemia or excessive exogenous steroids.

In some embodiments, and ODF may include a coloring agent to provide a visual indication of when the ODF dissolves and also a visual indication of which of the oral mucosa has been treated for easier identification of a treated area. Coloring agents may include, for example, a substance that allows a practitioner to identify an area that has been treated by an active agent, such as an anesthetic, whereby an injection may be administered into the area that has been made numb by anesthetic.

Coloring agents may include any benign coloring that is visible to a practitioner who will administer an injection. Accordingly, coloring agents may include by way of non-limiting example, natural pigments derived from natural sources such as vegetables, minerals or animals. Including: annatto, beet extract, caramel, beta-carotene and grape skin extract.

Other examples of coloring agents may include: Caramel coloring (E150), or other coloring made from caramelized sugar; Annatto (E160b), a reddish-orange dye or other coloring made from the seed of the achiote; Chlorophyllin (E140), a green dye or other coloring made from chlorella algae; Cochineal (E120), a red dye or other coloring derived from the cochineal insect, Dactylopius coccus; Betanin (E162) or other coloring extracted from beets; Turmeric or other coloring derived from curcuminoids, E100; Saffron or other coloring derived from carotenoids, E160a; Paprika (E160c); Lycopene (E160d); Elderberry juice; Pandan a green coloring or other coloring derived *Pandanus amaryllifolius*; Butterfly pea a blue dye or other coloring derived from *Clitoria ternatea*.

Other Coloring agents may include coloring approved under the Pure Food and Drug Act including, but not limited to: FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glace cherries); FD&C Yellow No. 5—Tartrazine, E102 (yellow shade); and FD&C Yellow No. 6—Sunset Yellow FCF, E110 (orange shade).

In some preferred embodiments, the ODF with an active agent includes a film that is colored, so that when the ODF dissolves, the treated oral mucosa is easily identified.

The ODF may also be stored in aseptic packaging, limiting cross contamination and include flavoring which is pleasant to taste.

In some embodiments, exemplary ODFs may contain film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

Additional ingredients that may be included in various embodiments include one or more of: plasticizers, sweetening and flavoring agents, coloring agents, saliva-stimulating agents, and thickening agents. In some preferred embodiments, inactive ingredients may include: Methocel K3, Methocek K100, Methocel K4, Sodium Carboxymethyl Cellulose, Glycerine, Sucralose, Polysorbate 80, Peppermint Oil Flavor, Gum Arabic, and Sodium Copper Chlorophylin.

Active agents may also include, for example a vitamin treatment, a nutraceutical, a nutrient, an antimicrobial or antibacterial agent.

EXAMPLES

In vitro and in vivo studies were conducted to gauge the effectiveness of a novel oral mucosa adhesive, moderately water-soluble, pliant polymer artificial dentifrice (AD) film containing dibucaine (DC) for relief of pain due to oral erosion. The film was prepared from a hydroxypropyl cellulose-M (HPC-M) ethanol solution containing varying amounts of DC, as well as polyethylene glycol.

In the in vitro experiments, the disintegration of HPC-M showed a lag time of about 50 min, a much lower rate than that of drug release, which more or less leveled off after 50 min. Twenty-five percent of the DC was released from the film (0.113 and 0.225 mg/cm2) after the initial 5 min, which then reached about 80% after 50 min, the time at which the polymer began to break up. In the in vivo study, the local anesthetic effect of the film was evaluated in 23 patients (10 males, 13 females) suffering from the adverse effects of chemotherapy. When applied to the wet surface of the mucosa, the AD film absorbed moisture and showed excellent adhesion. Pain relief in patients lasted 2.2+/−0.21 and 4.3+/−0.25 h at DC doses of 0.113 and 0.225 mg/cm2, respectively. These results suggest that the AD film may cover mucositis sites of oral mucosa long enough to allow DC release and bring relief from pain arising from chemotherapy and/or radiotherapy.

2. Pediatr Dent. 2001 Jan-Feb;23(1):11-4.

Comparison of topical EMLA 5% oral adhesive to benzocaine 20% on the pain experienced during palatal anesthetic infiltration in children.

Primosch R E, Rolland-Asensi G.

Department of Pediatric Dentistry, University of Florida College of Dentistry, Gainesville, Fla., USA. rprimosch@dental.ufl.edu Example 1

PURPOSE: The purpose of this investigation was to compare the pain responses of children during local anesthetic infiltration at bilateral palatal sites prepared with the topical application of benzocaine 20% oral adhesive (Orabase-B) versus benzocaine 20% gel (Hurricaine) or EMLA 5% oral adhesive (EMLA 5% cream in Orabase Plain).

METHODS: Forty subjects, aged 7-15 years old, received bilateral palatal injections following topical application of anesthetic agents applied in a randomized, crossover design. Pain responses were compared based upon subject self-report using a visual analogue scale (VAS), changes in the subject's heart rate, and operator assessment using a modified Children's Hospital of Eastern Ontario Pain Scale (CPS) that rated behavioral changes in children. Following the injections, the subjects were asked to choose which agent was preferred based on comfort and taste acceptance.

RESULTS: All the agents tested were equivalent in injection pain response comparisons, but Hurricaine had a slight

Example 2

Clinical evaluation of MGI 209, an anesthetic, film-forming agent for relief from painful oral ulcers associated with chemotherapy.

LeVeque F G, Parzuchowski J B, Farinacci G C, Redding S W, Rodu B, Johnson J T, Ferretti G A, Eisenberg P D, Zimmer M B.

Harper Hospital, Detroit, Mich. 48201.

PURPOSE: This open-label, multicenter trial evaluated the efficacy of a muco-adherent, anesthetic medication (MGI 209) for relief from painful oral ulcers associated with cytotoxic chemotherapy.

PATIENTS AND METHODS: Twenty-eight eligible cancer patients who had up to five discrete oral ulcers (total area < or =5 m2) completed this study. Mean age was 53.5 years (range, 21 to 81). Subjective assessments of oral discomfort before and after an orange juice pain challenge (OJPC), which was measured using a visual analog scale (VAS), and visual estimates of the amount of MGI 209 that remained on treated ulcers were collected at (1) baseline (before MGI 209 treatment); and (2) 30, 60, 120, and 180 minutes post treatment.

RESULTS: Most subjects had low VAS scores (4 or less), which was indicative of oral discomfort, at baseline before and after the OJPC. At 30, 60, 120, and 180 minutes after MGI 209 treatment, most subjects had high VAS scores before and after an OJPC compared with baseline scores, which was indicative of a substantial increase in oral comfort; these differences were statistically significant (P<0.0001). Mean percent of MGI 209 estimated to remain on ulcers at the previously mentioned times was 93.7%, 90.3%, 79.6%, and 71.3% of the total amount applied, respectively.

Example Conclusion: Benzocaine hydrochloride in combination with the protective, muco-adherent film-coating relieved discomfort for at least 3 hours even with exposure to an irritating beverage. MGI 209 treatment should allow patients with chemotherapy-induced oral ulcers to drink and eat with significantly diminished pain or no pain.

CONCLUSION

The present invention, as described above and as further defined by the claims below, provides methods of administering an active agent to a localized mucous membrane in the oral cavity of a mammal, as well as ODR formed therefore. The exemplary style of describing is not meant to limit the scope of the invention and the invention is therefore more clearly described and limited by the claims below.

What is claimed is:

1. A device for relieving pain during a procedure on a specific area of a mammalian mucous membrane, the device comprising:
   an oral dissolving film comprising a non-toxic film of a suitable size and shape to be placed on the specific area of the mammalian mucous membrane in a mammalian oral cavity and which dissolves essentially in its entirety as a result of contact with secretions from the mucous membrane in the mammalian oral cavity;
   a local anesthetic active agent combined with the oral dissolving film such that the local anesthetic active agent comes into contact with the specific area of the mammalian mucous membrane in the mammalian oral cavity as the oral dissolving film dissolves and thereby treats a situs to receive the procedure; and
   a coloring agent also combined with the oral dissolving film such that the coloring agent comes into contact with tissue in the specific area of the mammalian mucous membrane in the mammalian oral cavity as the oral dissolving film dissolves on the mammalian mucous membrane.

2. The device for relieving pain during the procedure on a specific site on the mammalian mucous membrane of claim 1, wherein the local anesthetic active agent combined with the oral dissolving film comprises a sufficient quantity to numb the specific area such that pain from procedure comprising an injection is diminished during administration of the injection.

3. The device for relieving pain during the procedure on a specific site on the mammalian mucous membrane of claim 1 wherein the coloring agent comprises a sufficient quantity to visibly mark the specific area as the oral dissolving film contacts the specific area.

4. The device for relieving pain during the procedure on a specific site on the mammalian mucous membrane of claim 1 wherein the coloring agent comprises a sufficient quantity to visibly mark the specific area after the oral dissolving film is fully dissolved.

5. The device for relieving pain during the procedure on a specific site on the mammalian mucous membrane of claim 1 wherein the local anesthetic active agent comprises ethyl ester of p-aminobenzoic acid.

6. The device for relieving pain during the procedure on a specific site on the mammalian mucous membrane of claim 1 wherein the local anesthetic active agent comprises lidocaine.

7. The device for relieving pain during the procedure on a specific site on the mammalian mucous membrane of claim 1 additionally comprising a sweetener.

8. The device for relieving pain during the procedure on a specific site on the mammalian mucous membrane of claim 1 wherein the oral dissolving film comprises hydroxypropylmethyl cellulose.

9. The device for relieving pain during the procedure on a specific site on the mammalian mucous membrane of claim 1 wherein the oral dissolving film comprises hydroxypropyl cellulose.

10. The device for relieving pain during the procedure on a specific site on the mammalian mucous membrane of claim 1 wherein the oral dissolving film comprises pullulan.

11. The device for relieving pain during the procedure on a specific site on the mammalian mucous membrane of claim 1 wherein the oral dissolving film comprises polyvinyl acetate.

12. The device for relieving pain during the procedure on a specific site on the mammalian mucous membrane of claim 1 wherein the oral dissolving film comprises Methocel K3, Methocek K100, Methocel K4 and Sodium Carboxymethyl Cellulose.

13. The device for relieving pain during the procedure on the specific site on the mammalian mucous membrane of claim 12 wherein the oral dissolving film additionally comprises Glycerine, Sucralose, Polysorbate 80 and Peppermint Oil Flavor.

14. The device for relieving pain during the procedure on the specific site on the mammalian mucous membrane of claim 13 wherein the oral dissolving film additionally comprises Gum Arabic and Sodium Copper Chlorophylin.

15. The device for relieving pain during the procedure on a specific site on the mammalian mucous membrane of claim 1 wherein the local anesthetic active agent comprises tetracaine.

16. The device for relieving pain during the procedure on the specific site on the mammalian mucous membrane of claim 15 wherein a visual indicator remains visible on an area of oral mucosa after the oral dissolving film dissolves essentially in its entirety.

17. The device for relieving pain during the procedure on the specific site on the mammalian mucous membrane of claim 16 wherein the visual indicator allows a practitioner to visually identify the area that has been treated by the local anesthetic and administer an injection into the area that has been treated by the local anesthetic with the oral dissolving film essentially dissolved in its entirety.

18. The device for relieving pain during the procedure on a specific site on the mammalian mucous membrane of claim 1 additionally comprising an aseptic package encompassing one or more oral dissolving films.

19. A device for relieving pain relating to a condition on a specific area of mammalian mucous membrane, the device comprising:

an oral dissolving film comprising a non-toxic film of a suitable size and shape to be placed on the specific area of the mammalian mucous membrane of a mammalian oral cavity and which dissolves essentially in its entirety as a result of contact with secretions from the mucous membrane in the mammalian oral cavity;

a local anesthetic active agent combined with the oral dissolving film such that the local anesthetic active agent comes into contact with the specific area of mammalian mucous membrane in the mammalian oral cavity as the oral dissolving film dissolves and treats a situs of discomfort comprising the specific area of mammalian mucous membrane; and a coloring agent also combined with the oral dissolving film such that the coloring agent comes into contact with tissue in the specific area of mammalian mucous membrane in the mammalian oral cavity as the oral dissolving film dissolves on the mammalian mucous membrane.

* * * * *